US012685680B2

(12) United States Patent　　(10) Patent No.:　US 12,685,680 B2
Hames et al.　　　　　　　　　　(45) Date of Patent:　　　Jul. 21, 2026

(54) LIGHT WEIGHT CLIP TO PROVIDE ADJUSTABLE TIE DOWN POINT FOR BANDAGE TO ENABLE PRESSURE TO BE APPLIED TO INGUINAL WOUNDS

(71) Applicant: Hames Industries LLC, North Wales, PA (US)

(72) Inventors: Robert Evan Hames, North Wales, PA (US); Ralph Edward DiLemmo, Norristown, PA (US)

( * ) Notice:　Subject to any disclaimer, the term of this patent is extended or adjusted under 35 U.S.C. 154(b) by 122 days.

(21) Appl. No.: 18/450,116

(22) Filed:　　Aug. 15, 2023

(65)　　　　Prior Publication Data

US 2024/0058183 A1　　Feb. 22, 2024

Related U.S. Application Data

(60) Provisional application No. 63/398,708, filed on Aug. 17, 2022.

(51) Int. Cl.
A61F 15/00　　　(2006.01)
(52) U.S. Cl.
CPC ................................. A61F 15/006 (2013.01)
(58) Field of Classification Search
CPC .............. A61B 17/132; A61B 17/1322; A61B 17/1325; A61B 17/1327; A61B 11/04; A61F 15/006; A61F 15/007; A61F 15/005; A61F 5/24–34; A61F 5/21; A61F 13/01; A61F 13/0102; A61F 13/82; A61F 13/80; A61F 13/74; A61F 13/665; A61F 13/66; A61F 13/64; A61F 13/62; A61F 13/47; A61F 13/474; A61F 13/476;
(Continued)

(56)　　　　References Cited

U.S. PATENT DOCUMENTS 501,563　A　*　7/1893　Gaines ..................... A61F 13/64
　　　　　　　　　　　　　　　　　604/397
909,948　A　*　1/1909　Schmertz .................. A61F 5/40
　　　　　　　　　　　　　　　　　602/73
(Continued)

OTHER PUBLICATIONS

PCT International Search Report, Application No. PCT/US2023/072376, Mar. 1, 2024 (4 pages).
(Continued)

*Primary Examiner* — Rachael E Bredefeld
(74) *Attorney, Agent, or Firm* — Douglas J. Ryder; Ryder, Mazzeo & Konieczny LLC

(57)　　　　　　ABSTRACT

One or more clips to be hooked to an item (e.g., belt) and enable a bandage wrapped around an inguinal wound to be secured thereto. The clip(s) act as tie-down point(s) for the bandage to provide most efficient pressure to the wound. The clips include a waist securing member and a bandage retention member. The waist securing member includes first and second legs secured together along a first side (e.g., top) of clip by a first connection piece. A first space is defined between adjacent sides of first and second legs having a first opening along a second side (e.g., bottom) of clip. The bandage retention member includes second and third legs secured together along the second side of the clip by a second connection piece. A second space is defined between adjacent sides of second and third legs having a second opening along the first side of clip.

4 Claims, 10 Drawing Sheets

(58) Field of Classification Search
CPC .... A61F 13/505; A61F 13/5605; A61F 13/56;
Y10T 24/3485; Y10T 24/4091; Y10T
24/4088
USPC ........................ 602/79, 71; 24/198; 128/95.1
See application file for complete search history.

(56) References Cited

U.S. PATENT DOCUMENTS

| | | | | |
|---|---|---|---|---|
| 1,768,977 | A * | 7/1930 | Ealy | A61F 13/64 |
| | | | | 24/570 |
| 2,224,626 | A * | 12/1940 | Marcus | A61F 13/64 |
| | | | | 24/200 |
| 2,320,067 | A * | 5/1943 | Caughren | A01M 31/006 |
| | | | | 224/268 |
| 2,333,839 | A * | 11/1943 | Blackburn | A61F 13/64 |
| | | | | 2/244 |
| 2,854,973 | A * | 10/1958 | Jackson | A61F 13/64 |
| | | | | 128/891 |
| 3,155,298 | A * | 11/1964 | Brown | A45D 44/06 |
| | | | | 24/3.12 |
| 3,342,184 | A * | 9/1967 | Joa | A61F 13/64 |
| | | | | 604/366 |
| 4,586,499 | A | 5/1986 | Kaletzky | |
| 4,974,764 | A | 12/1990 | Cantwell | |
| 5,514,155 | A | 5/1996 | Daneshvar | |
| 6,384,294 | B1 * | 5/2002 | Levin | A61F 13/069 |
| | | | | 602/44 |
| 2015/0342803 | A1 | 12/2015 | Julian et al. | |

OTHER PUBLICATIONS

PCT Written Opinion of the International Search Authority, Application No. PCT/US2023/072376, Mar. 1, 2024 (7 pages).

* cited by examiner

LIGHT WEIGHT CLIP TO PROVIDE ADJUSTABLE TIE DOWN POINT FOR BANDAGE TO ENABLE PRESSURE TO BE APPLIED TO INGUINAL WOUNDS

BACKGROUND

Certain wounds result in excessive bleeding. The bleeding must be stopped to prevent a patient from bleeding out. An initial step is often to pack the wound and then apply pressure to the packed wound to stop the flow of blood. The pressure may often be applied by wrapping an item (e.g., cloth, bandage, strap, belt) tightly around the body part where the wound is located. Wounds in the groin region (inguinal wounds) are a complex style of wound that requires fast identification and treatment. FIGS. 1A-B illustrate a front and a cross-sectional view of a patient's body 100 having an inguinal wound 110. The wound 110 is located below the patient's waist 120 in proximity to their right leg 130 (shown on left).

The location of the inguinal wound 110 makes the application of a tourniquet difficult. FIGS. 2A-D illustrate a series of front views of the patient 100 with the inguinal wound 110 being treated based on current practices in the United States Military. As illustrated in FIG. 2A, an initial step is to pack the wound with combat gauze 200. The patient's belt 210 is then tightened and a cloth 220 is placed under the belt 210 along the right leg 130 (the leg closest to the wound) as shown in FIG. 2B. An elastic bandage 230 is wrapped around the right leg 130 to apply pressure to the gauze bandage 200 over the wound and over the cloth 220 as shown in FIG. 2C. The cloth 220 is then cinched upwards by tying it to a tightened belt 210 to create upwards pressure on the groin as shown in FIG. 2D. The procedure is rather complex and is taught to medical personnel to ensure proper pressure and stabilization. This method has limited effectiveness since the bandage wrap 230 will almost always have pressure applied from a single point (on an appropriate leg) 240 created by the cloth 220 being tied to a point on the belt 210 (waistline) aligned with a far point of the appropriate leg of the patient.

There are other ways of applying pressure, like through mechanisms that wrap around the waist and use mechanical leverage or pneumatics to stop bleeding or hemorrhaging. These apparatuses can usually also apply pressure to wounds that are not easily reachable with the previously mentioned bandaging method. They do typically weigh more and take up more space than the materials used in the standard method and also require special training to use effectively. These larger, more complex devices are difficult to maintain in place when a casualty needs to be moved, which makes them less than ideal for field conditions, and more suited for levels of care higher than the emergency responder/medic.

What is needed is a means of stopping inguinal hemorrhaging that is easy to implement, does not require any expensive or heavy equipment, which provides pressure where required, and can maintain the pressure during movement of the patient.

BRIEF DESCRIPTION OF THE DRAWINGS

The structure, objects, and advantages of the releasable tie will be understood by referring to the detailed description of illustrative embodiments in conjunction with the accompanying technical drawings, in which.

DETAILED DESCRIPTION

Figures 1A, 1B:
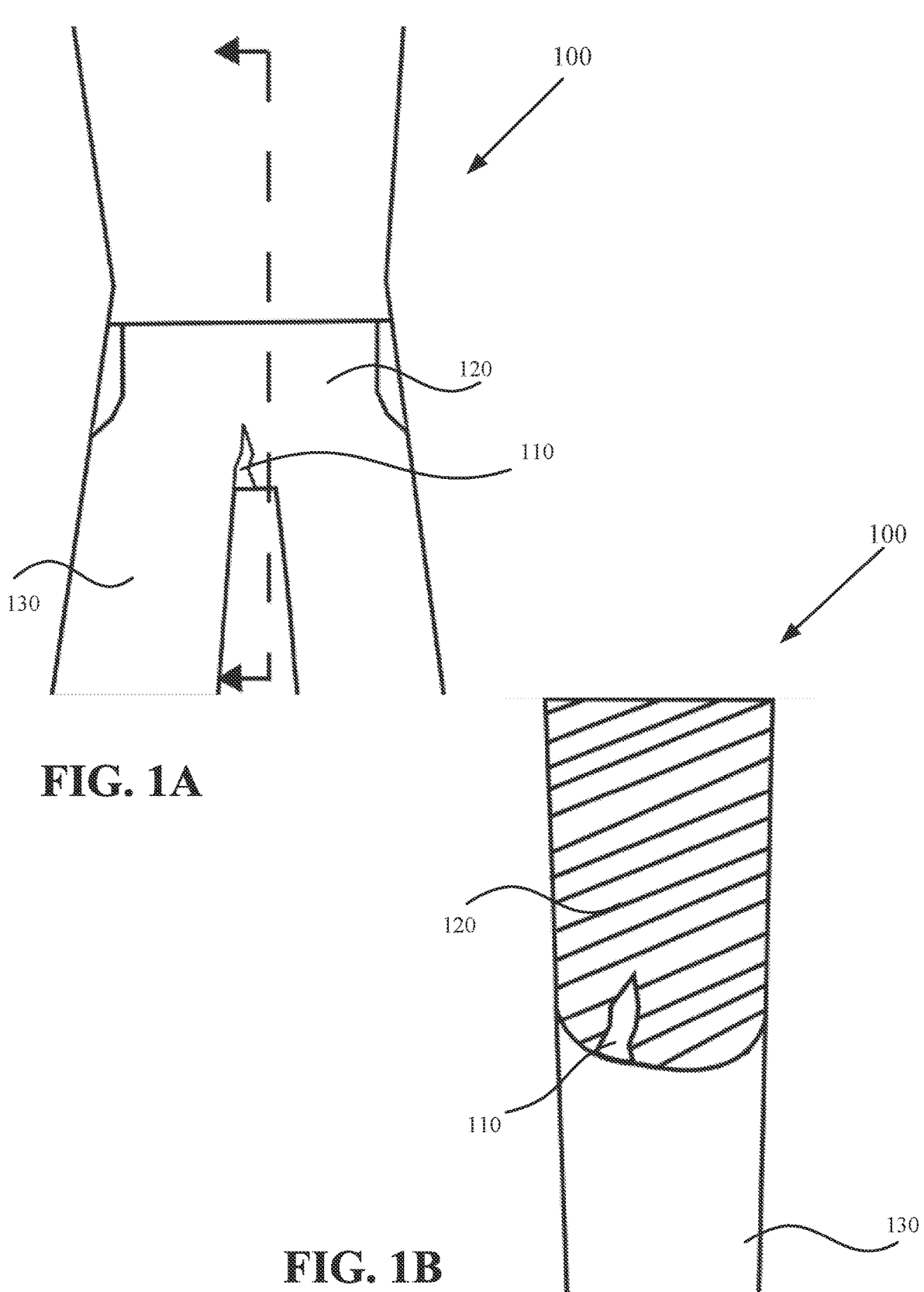
FIGS. 1A-B illustrate a front and a cross-sectional view of a patient's body having an inguinal wound.
Figures 2A, 2B:
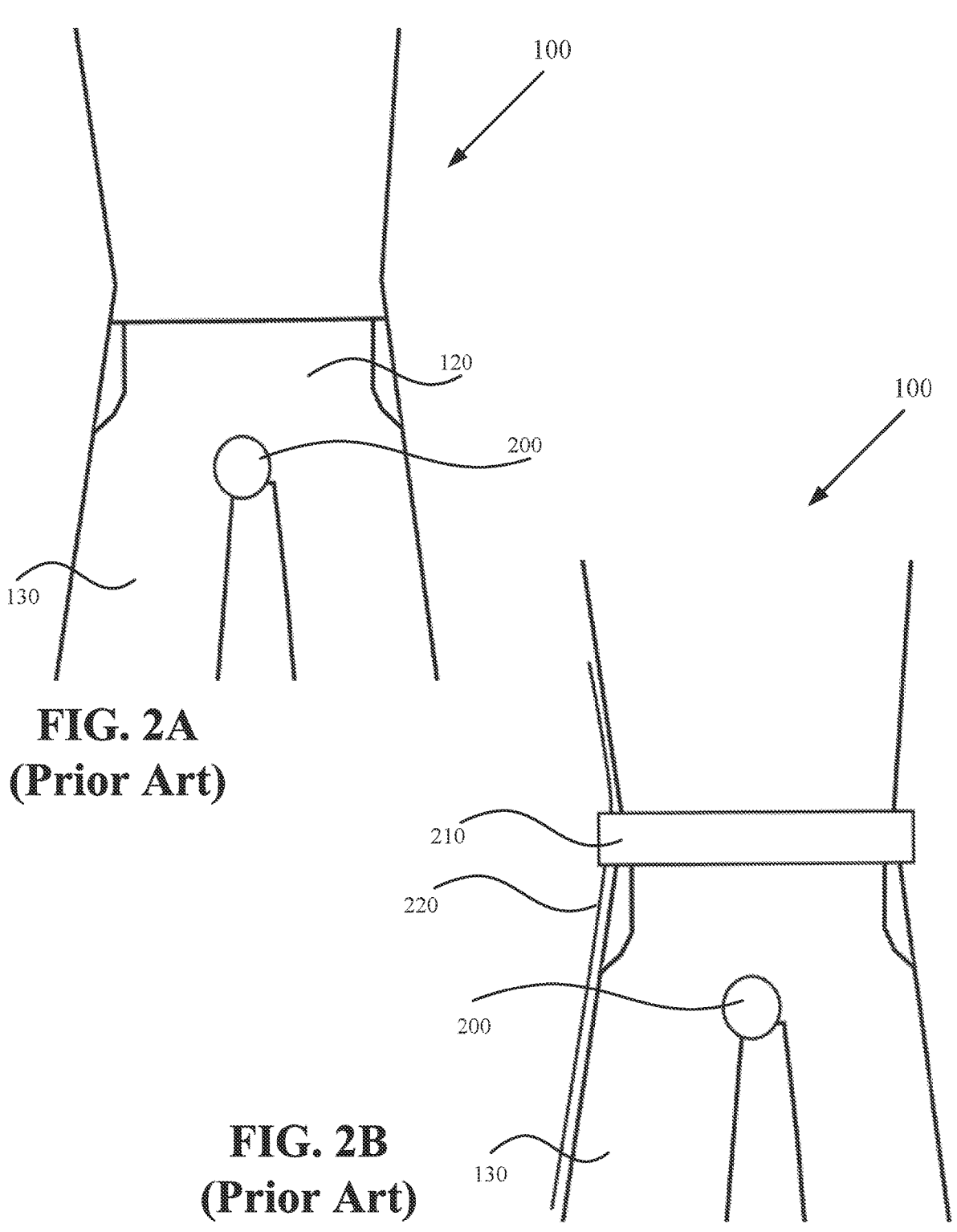
FIGS. 2A-D illustrate a series of front views of a patient with an inguinal wound being treated based on current practices in the United States Military.
Figures 2C, 2D:
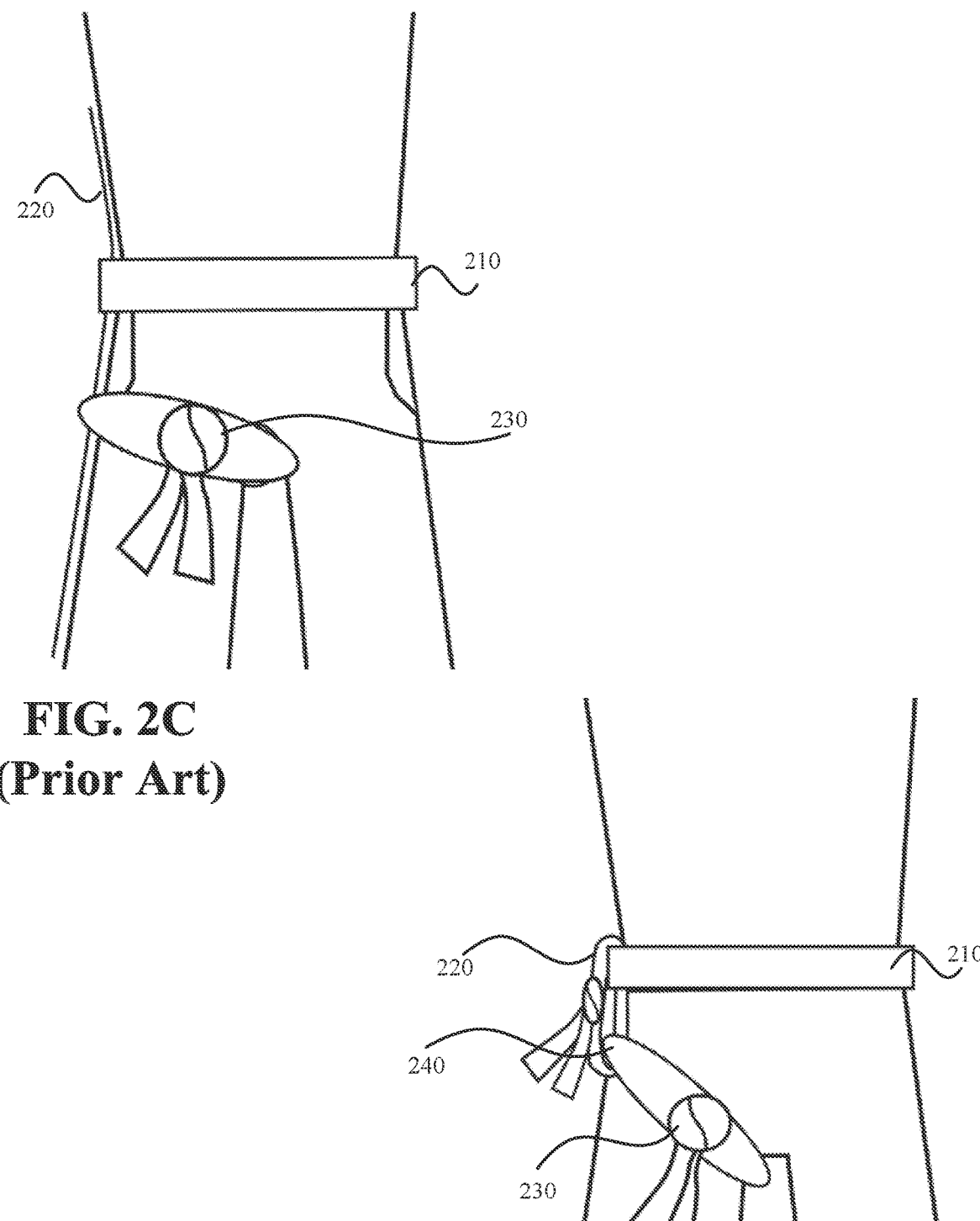
Figures 3A, 3B:
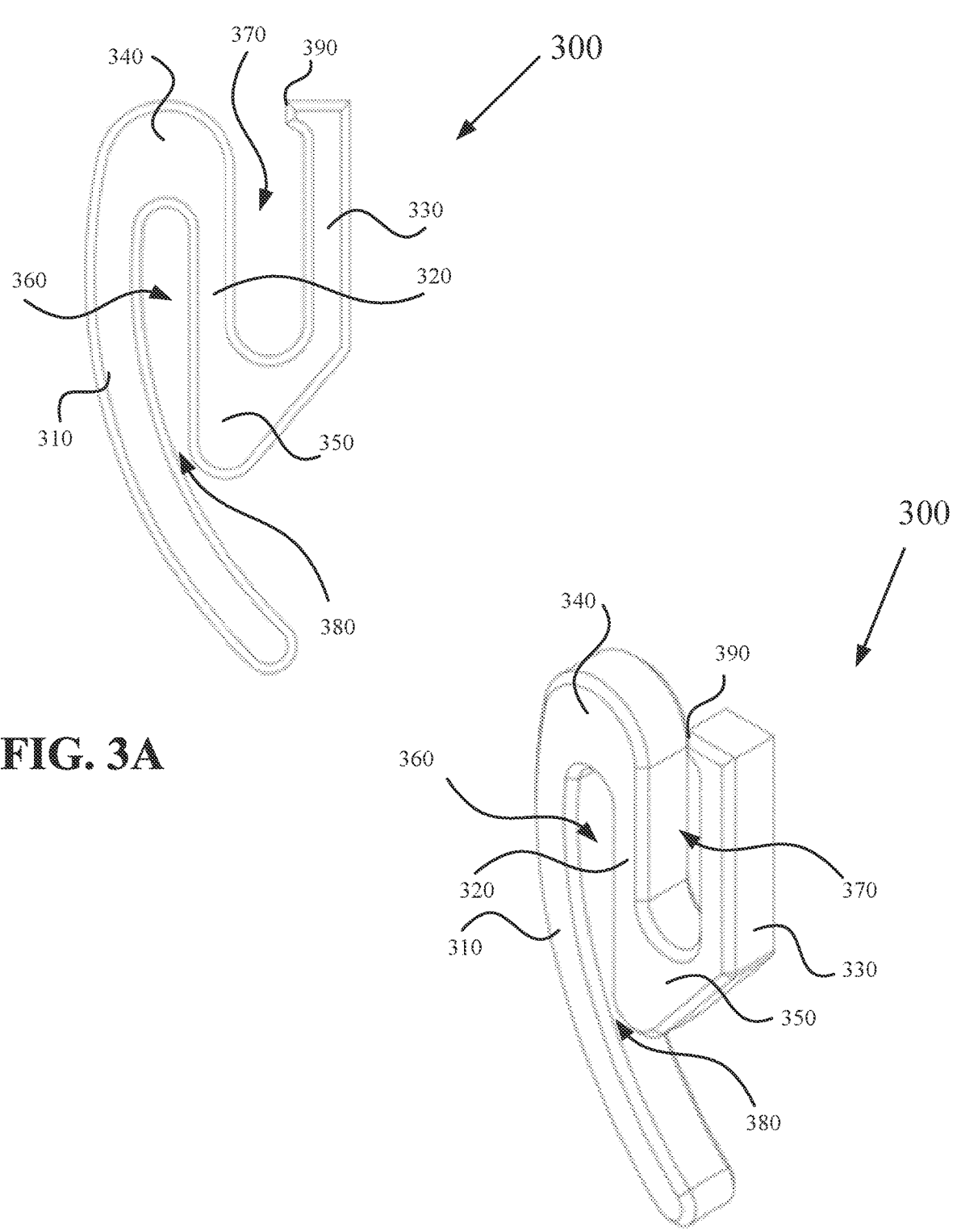
FIGS. 3A-D illustrate various views of an example clip, according to one embodiment.
Figures 3C, 3D:
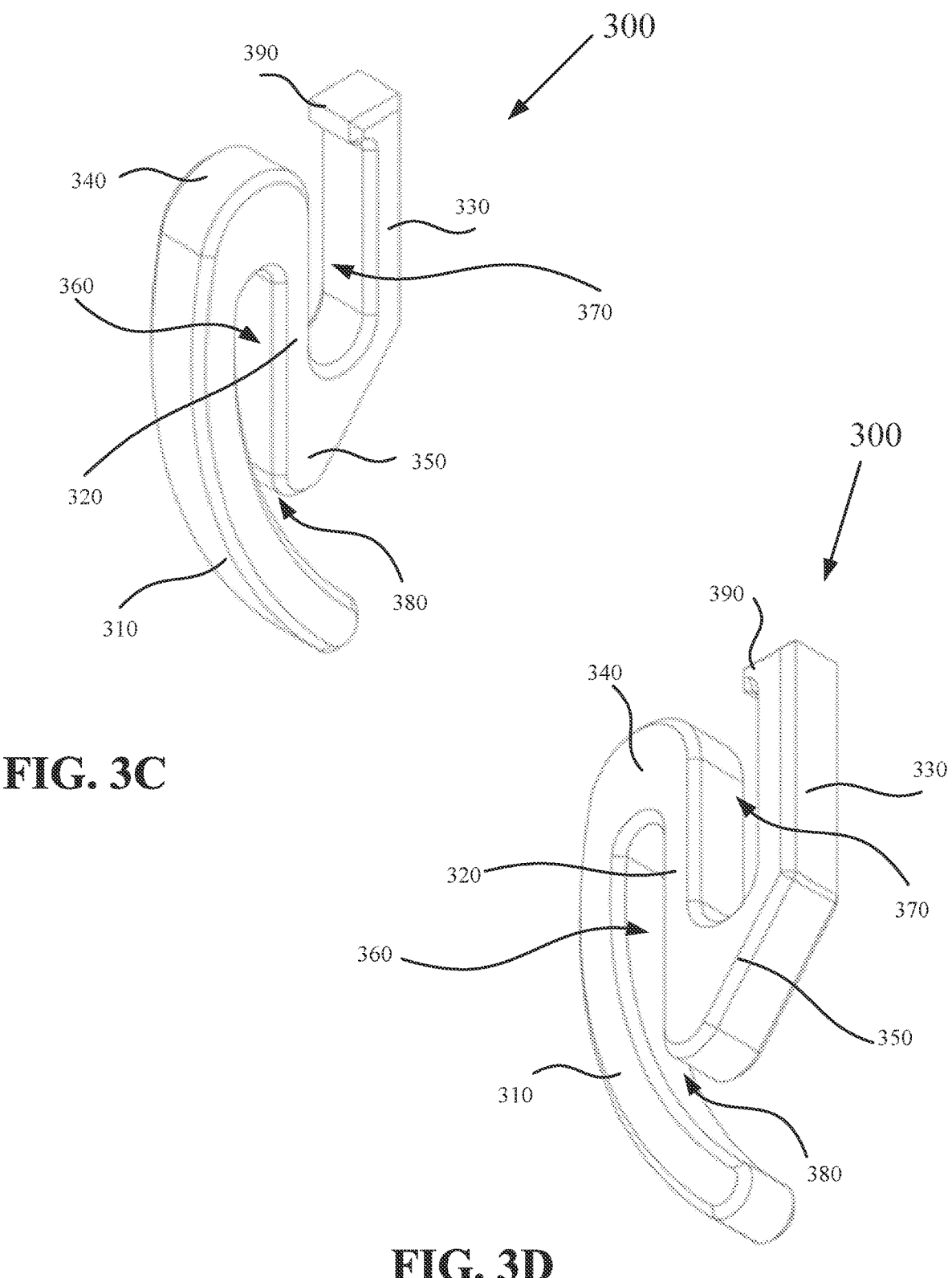

A clip designed to be hooked around a patient's waist and to enable an elastic (or inelastic) bandage to be secured thereto in order to apply pressure to an inguinal wound. The clip may be hooked to a patient's clothing covering their lower body (e.g., pants, shorts, skirt). For ease of discussion, the clothing will simply be referred to as pants. The clip may be clipped to items secured to hold their pants up around the waist including a belt or other garments wrapped therearound including, but not limited to, slings, bandanna, and triangle bandage. For ease of discussion, the item holding the pants up will simply be referred to as a belt. The clip acts as a tie-down point for a bandage wrapped around the wound to apply pressure to the wound and to secure the gauze that has been applied to the wound. The location of the clip defines the tie-down point so movement of the clip enables the tie down point to be located where it will apply the most efficient pressure to the wound. That is, using the clip does not limit the tie down point to basically the same point as with the method described with respect to FIGS. 2A-D.

The use of a clip enables a first responder or medic to apply constant and stable pressure to a wound without special training or having to carry a larger apparatus. A single clip or multiple clips could be used, and they can be positioned anywhere (e.g., any point and in any direction in the groin area) around the patient's waist to ensure pressure is applied at the best location for the wound.

FIGS. 3A-D illustrate various views of an example clip 300 that can be used to hook to, for example, a patient's pants, around their waist and to enable a bandage to be secured thereto. The clip 300 includes first, second and third legs 310, 320, 330, a first connection piece 340 and a second connection piece 350. The first connection piece 340 connects a first side (e.g., top) of the first and the second legs 310, 320 and provides a first space 360 therebetween. Entry to the first space 360 is between a second side (e.g., bottom) of the first and the second legs 310, 320. The second connection piece 350 connects the second side (e.g., bottom) of the second and the third legs 320, 330 and provides a second space 370 therebetween. Entry to the second space 370 is between the first side (e.g., top) of the second and the third legs 320, 330.

The first leg 310 is curved toward the second leg 320 as it extends from the first side (top) to the second side (bottom). The curved first leg 310 will extend away from a user when the clip 300 is secured to the waist of a patient's pants or their belt. The curving away from the patient's body will help prevent the first leg 310 from digging into the patient's skin when downward force is applied to the clip 300. The curved first leg 310 allows a first responder to place the clip 300 anywhere on the patient without the clip 300 digging into the patient's skin. The curved first leg 310 also provides a narrow entry point 380 to the first space 360. The narrow entry point 380 provides a pinch point that clamps down on the waistband of the pants or belt of a patient when in use to prevent the clip 300 from sliding. The first leg 310, the first connection piece 340, the second leg 320, the first space 360 and the narrow entry (pinch) point 380 form the waist securing member (belt retention member) of the clip 300 that secures to the waist of a patient's pants or their belt.

The third leg 330 includes a protrusion (e.g., flange) 390 on the first end (top) thereof that extends toward the second leg 320. The flange 390 shrinks the entry to the second space 370 and is used to help secure a bandage wrapped around the third leg 330 within the second space 370. The third leg 330, the second connection piece 350, the second leg 320, the second space 370 and the flange 390 form a bandage retention member of the clip 300 that a bandage can be secured thereto. The bandage retention section allows a wrapped bandage to be captured in a radial or planar "pocket".

The first and second connection pieces 340, 350 may be wider than the first, second and third legs 310, 320, 330 to increase the strength of the clip 300 at these points as these points are the points most likely to break during use. For example, when a bandage is secured within the bandage retention section of the clip 300 and is then tightened the load applied to the clip 300 increases. The most significant amount of force is applied to the second connection piece 350 as the load on the third leg 330 increases (the third leg 330 is being pulled away). Likewise, if the clip 300 is secured onto pants and/or a belt that is too thick this will require the first space 360 to expand. The most significant amount of force applied because of this expansion will be to the first connection piece 340. The increase in the height and/or width increases the rigidity of the clip 300 and the safety thereof during use. The increased rigidity of the first and second connection pieces 340, 350 mitigates the impact of force that is applied thereto in use and enables additional bending to occur before damage or breakage occurs.

Figures 4A, 4B:
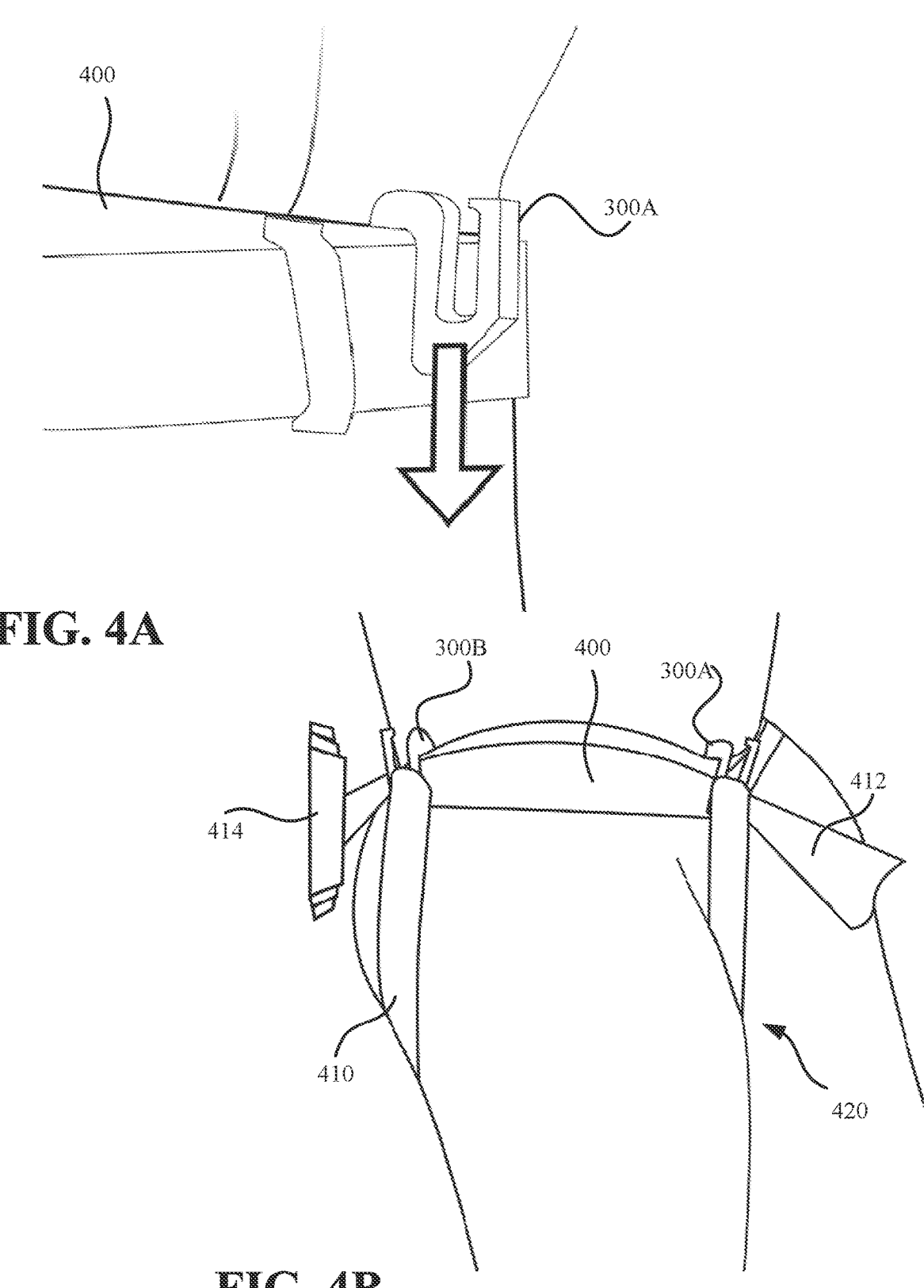
FIGS. 4A-D illustrate a series of different views showing the use of the clip to wrap an inguinal wound, according to one embodiment.

FIGS. 4A-D illustrate a series of different views showing the use of a pair of clips 300A, 300B to wrap an inguinal wound. FIG. 4A illustrates a front view of a clip 300A being secured to a belt 400 of a patient. To ensure the belt 400 provides the appropriate support, the belt 400 should be tightened around the patient's waist before the hook 300A is inserted thereover. If the patient does not have a belt 400, other garments (e.g., sling, bandanna, triangle bandage) may be wrapped around the waist of the patient's pants to provide the appropriate support. If the patient's pants are tight enough, the clip 300A may be secured directly to the pants. The clip 300A may be secured to the belt 400 by locating the first opening 360 over the belt and pushing the clip 300A downward so that the first leg 310 is located behind the belt 400. The clip 300A is pushed downward until the first connection piece 340 rests on the top of the belt 400. It should be noted that for ease of illustration, the parts of the clip 300A are not separately labeled.

FIG. 4B illustrates a side view of an elastic (or inelastic) bandage 410 being wrapped around the pair of clips 300A, 300B. A first end 412 of the bandage 410 is looped around the clip 300A. The bandage 410 then passes through the legs and around the groin 420 to secure the gauze (not illustrated)

covering the inguinal wound (not illustrated). The bandage 410 is then looped around the clip 300B. The flange 390 (not separately labeled) clearly would help secure the bandage 410 within the second space 370 (not separately labeled) of the clips 300A, 300B. A second end 414 of the bandage 410 extends past the clip 300B. While not illustrated in FIG. 4B, the second end 414 will pass through the legs and around the groin 420 again.

Figure 4C:
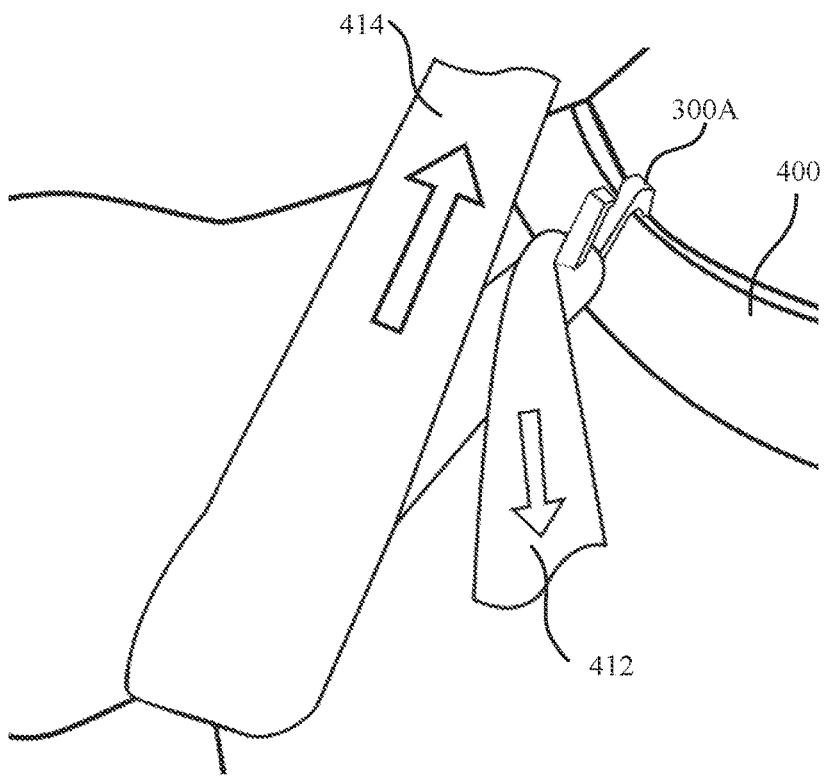
Figure 4D:
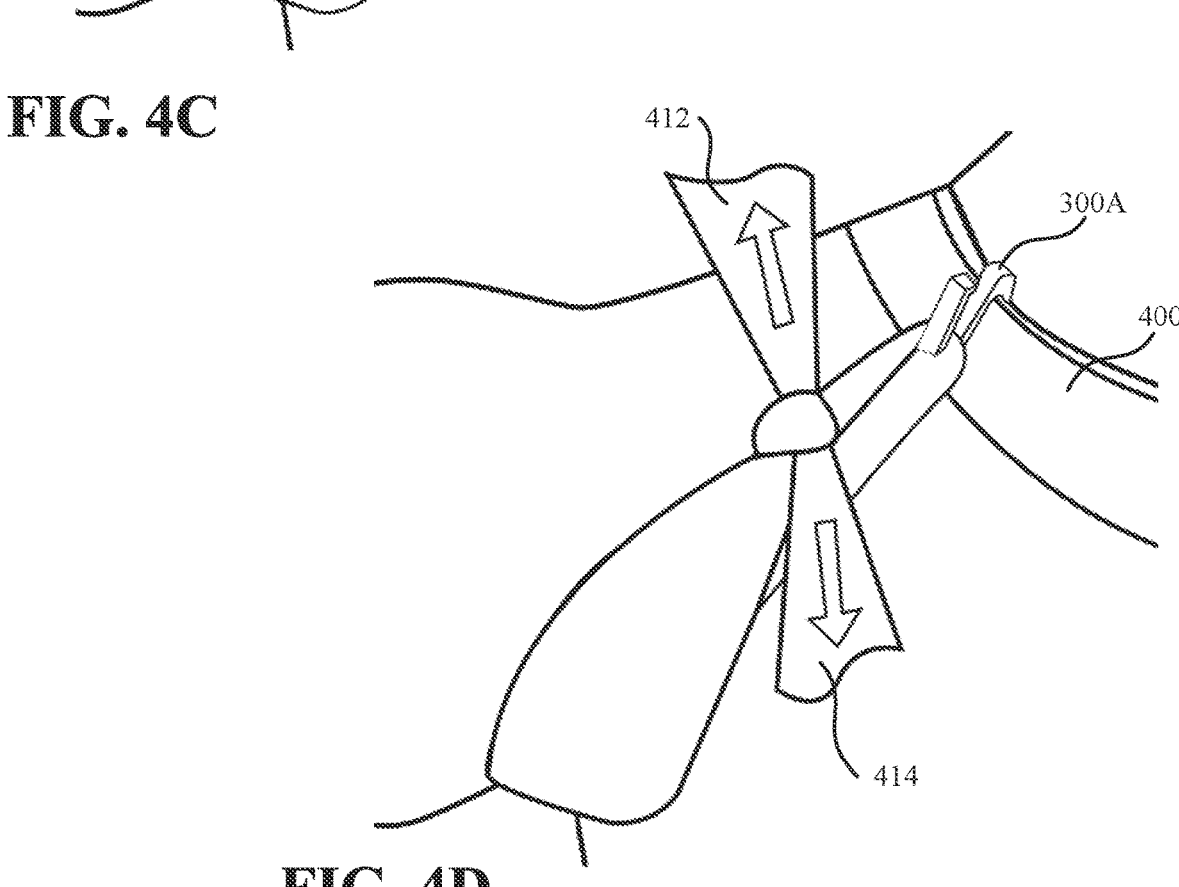

FIG. 4C illustrates a side view of the bandage 410 after being looped back over the groin of the patient. The first end 412 is pulled downward from the clip 300A and the second end 414 is pulled upward toward the clip 300A. FIG. 4D illustrates a side view of the bandage 410 after the two ends 412, 414 are tied together. The tying of the ends 412, 414 together is to ensure that the appropriate pressure is applied by the bandage 410.

Figures 5A, 5B:
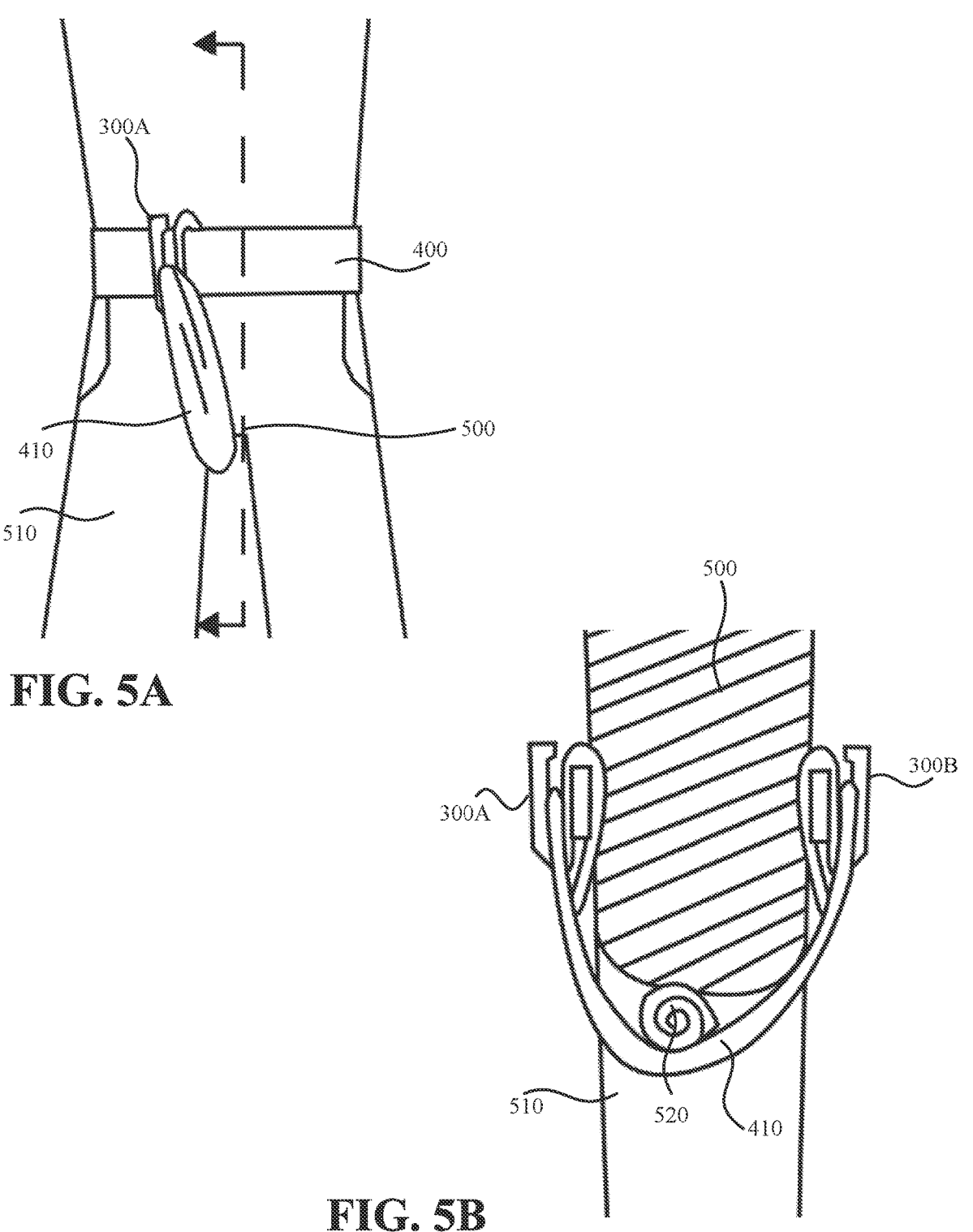
FIGS. 5A-B illustrate a front and a cross-sectional view of a pair of clips being used to secure the bandage that is wrapped around an inguinal wound, according to one embodiment.

FIGS. 5A-B illustrate a front and a cross-sectional view of the clips 300A, 300B being used to secure the bandage 410 that is wrapped around an inguinal wound (not visible). The bandage 400 traverses the groin 500 as it is wrapped around the clips 300A, 330B located on the patients belt 400. As the wound is in proximity to the patient's right leg 510 (shown on left), the clips 300A, 300B are secured on that side of the patient's waist. The clips 300A, 300B are secured on the front side and back side of the belt 400. The bandage 410 applies pressure to the gauze 520 covering the wound.

The invention is in no way intended to be limited to using a pair of clips, or the pair of clips being located in the front and back of the patient's waist as illustrated in FIGS. 5A-B. Rather, any number of clips could be utilized, and the clips could be located on any location around the waist without departing from the current scope. The number and location of the clips are selected to apply pressure to the inguinal wound.

Figures 6A, 6B:
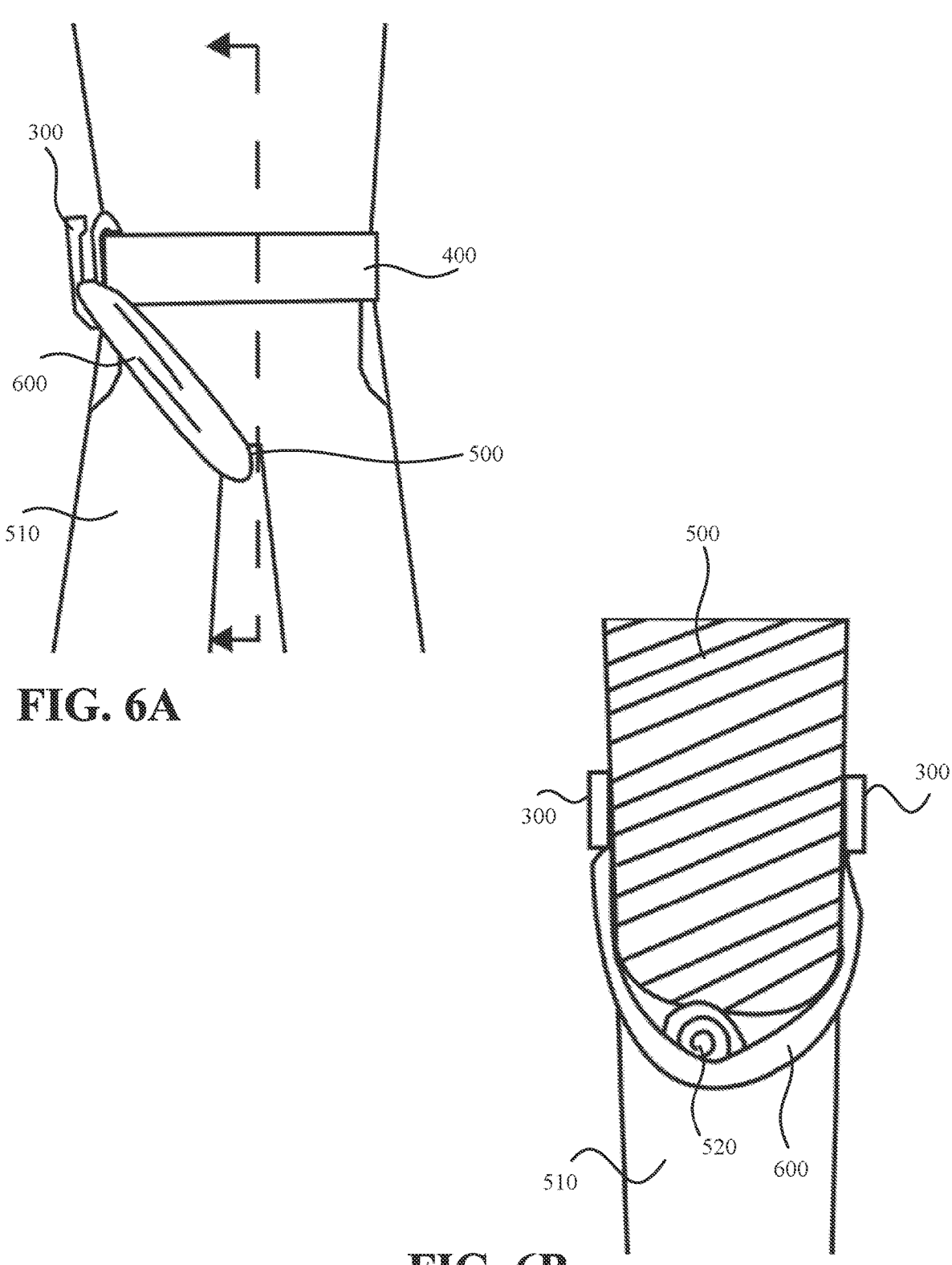
FIGS. 6A-B illustrate a front and a cross-sectional view of a single clip being used to secure a bandage that is wrapped around an inguinal wound, according to one embodiment.

FIGS. 6A-B illustrate a front and a cross-sectional view of a single clip 300 being used to secure a bandage 600 that is wrapped around an inguinal wound (not visible). The bandage 600 traverses the groin 500 as it is wrapped around the clip 300 located on the patients belt 400. As the wound is in proximity to the patient's right leg 510 (shown on left), the clip 300 is secured on the right side of the patient's belt 400. The bandage 600 applies pressure to the gauze 520 covering the wound. One end of the bandage 600 may be secured to the clip 300, the bandage 600 may be routed around the groin 500, the other end of the bandage 600 may be secured to the clip 300 and then the two ends may be tied together to apply the appropriate pressure. Alternatively, after a second end of the bandage 600 is secured to the clip 300, the bandage 600 may be routed around the groin 500 again and then the two ends may be secured. In fact, the bandage 600 could be routed over the groin 500 any number of times where it is secured to the clip 300 each time and then eventually the two ends are tied together.

It should be noted that the clip 300 is not limited to the illustrated example. Rather, the clip could vary in size, shape and configuration without departing from the current scope so long as the clip is capable of securing to the pants or belt of a patient, provides a means to secure a bandage thereto, prevents the clip from sliding during use and is rigid enough to not get damaged or break during use. For example, the first leg need not be curved to prevent the clip from digging into the patient. Rather, the leg could be shorter or could be angled outward in order to prevent the digging in. An angled outward first leg could also provide the pinch point, which is desired to prevent the clip from sliding. The third leg need not include a flange to help secure the bandage within the second opening. Rather, the third leg could be curved or angled back toward the second leg to provide a narrower opening to help secure the bandage therewithin.

Figure 7:
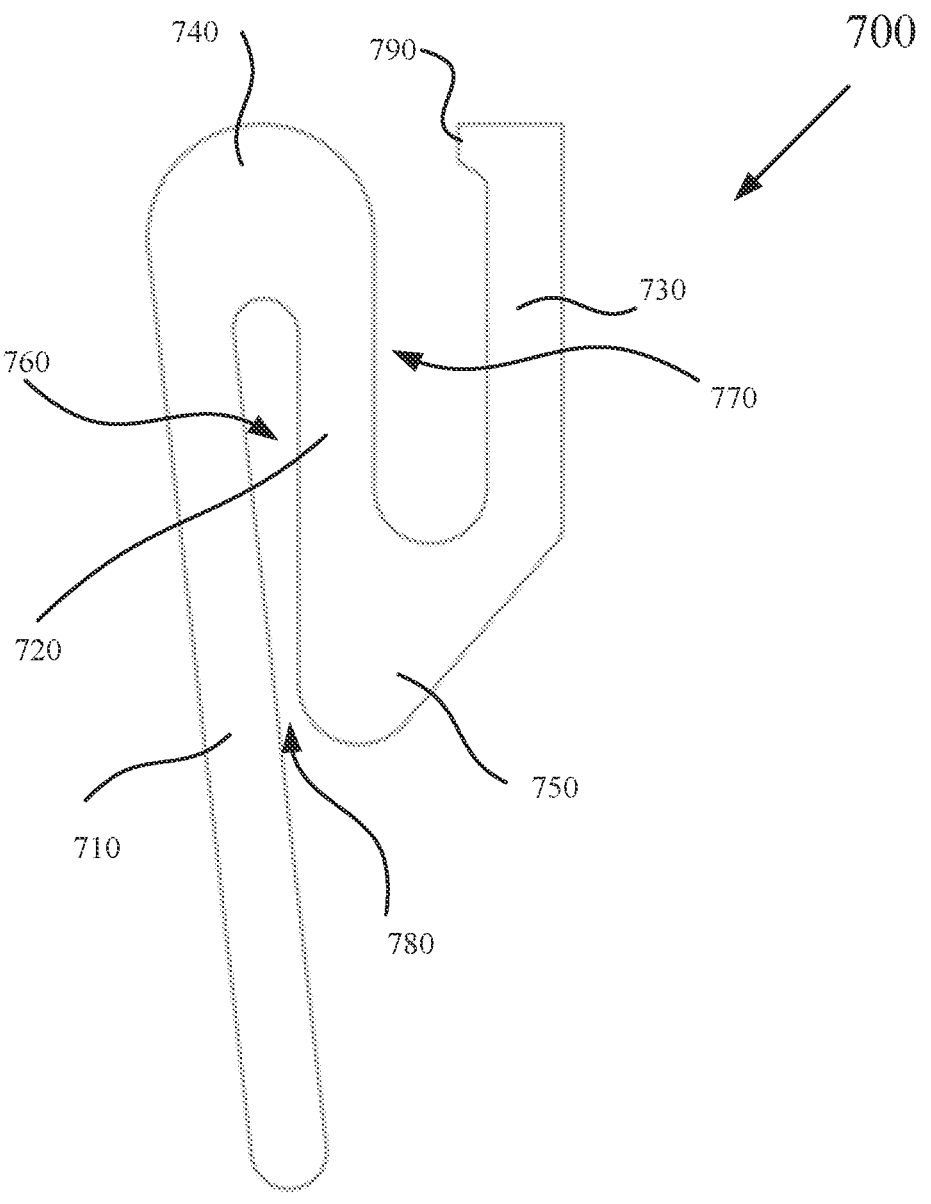
FIG. 7 illustrates a front view of an example clip that can be used to hook to the pants or belt of a patient and to enable a bandage to be secured thereto, according to one embodiment.

FIG. 7 illustrates a front view of an example clip 700 that can be used to hook to the pants or belt of a patient and to enable a bandage to be secured thereto. The clip 700 is similar to the clip 300 and includes first, second and third legs 710, 720, 730, a first connection piece 740 and a second connection piece 750. The first connection piece 740 connects a first side (e.g., top) of the first and the second legs 710, 720 and provides a first space 760 therebetween. Entry to the first space 760 is between a second side (e.g., bottom) of the first and the second legs 710, 720. The second connection piece 750 connects the second side (e.g., bottom) of the second and the third legs 720, 730 and provides a second space 770 therebetween. Entry to the second space 770 is between the first side (e.g., top) of the second and the third legs 720, 730.

The first leg 710 is straight but is angled toward the second side (bottom) of the second leg 720 as it extends from the first side (top) to the second side (bottom). The bottom of the angled first leg 710 extends away from a user when the clip 700 is secured to the waist of a patient's pants or their belt. This prevents the first leg 710 from digging into the patient's skin when force is applied by a bandage being secured thereto. The angled first leg 710 also provides a narrow entry point 780 to the first space 760 which provides a pinch point that clamps down on the pants or belt of a patient when in use to prevent the clip 700 from sliding.

The third leg 730 includes a protrusion (e.g., flange) 790 on the first end (top) thereof that extends toward the second leg 720. The flange 790 shrinks the entry to the second space 770 and is used to help secure a bandage wrapped around the third leg 730 within the second space 770.

The clips may be made of lightweight materials that provide the necessary strength. According to one embodiment, the clips (e.g., 300, 700) may be manufactured by injection molding. According to one embodiment, the clips (e.g., 300, 700) may be made of glass filled nylon. According to alternative embodiments, the clips may be made of any number of plastics. The clips could be made of carbon fiber but do not require the strength provided thereby or the cost associated therewith.

According to alternative embodiments, the clips may be manufactured by machining, casting, forging, laser/water cutting, stamping, 3D printing and extrusion. According to alternative embodiments, the clips may be made of any number of metals.

The clips are designed to be as small and compact as possible to minimize their footprint. The clips may be stored in a medic's aid bag. According to one embodiment, a kit may be provided that includes one or more clips as well as items that may be used with the clips (e.g., gauze, bandage, clotting agent).

Although the invention has been illustrated by reference to specific embodiments, it will be apparent that the invention is not limited thereto as various changes and modifications may be made thereto without departing from the scope. Reference to "one embodiment" or "an embodiment" means that a particular feature, structure or characteristic described therein is included in at least one embodiment. Thus, the appearances of the phrase "in one embodiment" or "in an embodiment" appearing in various places throughout the specification are not necessarily all referring to the same embodiment.

The various embodiments are intended to be protected broadly within the spirit and scope of the appended claims.

The invention claimed is:

1. A method for wrapping an inguinal wound of a patient, the method comprising:
retrieving necessary equipment including gauze, a bandage and a clip comprising:
a waist securing member including
a first leg, a second leg, and a first connection piece,
a first end of the first leg and a first end of the second leg are secured together by the first connection piece,
a first space is located between adjacent sides of the first leg and the second leg,
a second end of the first leg extends farther than a second end of the second leg,
a first opening to the first space is provided between the second end of the first leg and the second end of the second leg,
the first opening is smaller than the first space; and
a bandage retention member including
the second leg, a third leg, and a second connection piece,
the second end of the second leg and a second end of the third leg are secured together by the second connection piece,
the second leg and the third leg are substantially parallel to each other,
a second space is located between adjacent sides of the second leg and the third leg,
a flange is included on a first end of the third leg that extends in a direction towards the first end of the second leg;
a second opening to the second space is provided between the first end of the second leg and the flange located on the first end of the third leg, and
the second opening is smaller than the second space;
packing the inguinal wound with the gauze;
identifying an appropriate tie down point on a waist of the patient to apply efficient pressure to the inguinal wound;
securing the waist securing member of the clip to an item around a patient's waist at the appropriate tie down point;
securing a first end of the bandage to the bandage retention member of the clip;
routing the bandage around a groin of the patient to cover the inguinal wound;
securing a second end of the bandage to the bandage retention member of the clip; and
tying the first end of the bandage and the second end of the bandage together.

2. The method of claim 1, wherein the securing the waist securing member of the clip to an item includes securing the waist securing member of the clip to a belt around the patient's waist.

3. The method of claim 1, wherein the routing the bandage around a groin includes routing the bandage around the groin of the patient in a first direction to cover the inguinal wound, securing a middle portion of the bandage to the bandage retention member of the clip, and routing the bandage around the groin of the patient in a second direction to cover the inguinal wound.

4. The method of claim 1, wherein
the retrieving necessary equipment includes retrieving a pair of clips;
the identifying an appropriate tie down point includes identifying an appropriate pair of tie down points;
the securing the waist securing member of the clip to an item includes securing the waist securing member of a first clip to a first tie down point on the item and securing the waist securing member of a second clip to a second tie down point on the item;

the securing a first end of the bandage to the bandage retention member of the clip includes securing the first 5 end of the bandage to the bandage retention member of the first clip;

the routing the bandage around a groin of the patient includes routing the bandage around the groin of the patient in a first direction to cover the inguinal wound, 10 securing a middle portion of the bandage to the bandage retention member of the second clip, and routing the bandage around the groin of the patient in a second direction to cover the inguinal wound; and the securing a second end of the bandage to the bandage 15 retention member of the clip includes securing the second end of the bandage to the bandage retention member of the first clip.

* * * * *